(12) United States Patent
Foo et al.

(10) Patent No.: US 7,385,071 B2
(45) Date of Patent: Jun. 10, 2008

(54) HYDROCYANATION OF PENTENENITRILES AND/OR 2-METHYL-3-BUTENENITRILE USING PROMOTERS OBTAINED FROM THE CHLORINATION OF TITANIUM-RICH ORES

(75) Inventors: Thomas Foo, Wilmington, DE (US); Christian Peter Lenges, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 268 days.

(21) Appl. No.: 10/695,015

(22) Filed: Oct. 28, 2003

(65) Prior Publication Data

US 2005/0090681 A1    Apr. 28, 2005

(51) Int. Cl.
*C07C 253/10*    (2006.01)

(52) U.S. Cl. .................................................... 558/338
(58) Field of Classification Search ................. 558/338
See application file for complete search history.

(56) References Cited

U.S. PATENT DOCUMENTS

| 5,512,696 | A | * | 4/1996 | Kreutzer et al. | ............ 558/338 |
| 5,523,453 | A | * | 6/1996 | Breikss | ........................ 558/338 |

\* cited by examiner

*Primary Examiner*—James O. Wilson
*Assistant Examiner*—Ebenezer Sackey

(57) ABSTRACT

Process for hydrocyanating a substrate selected from 2-, 3-, or 4-pentenenitrile and/or 2-methyl-3-butenenitrile or mixtures thereof by contacting the substrate with HCN in the presence of a zero-valent nickel catalyst and a promoter that is obtained as a byproduct of titanium ore chlorination.

14 Claims, No Drawings

HYDROCYANATION OF PENTENENITRILES AND/OR 2-METHYL-3-BUTENENITRILE USING PROMOTERS OBTAINED FROM THE CHLORINATION OF TITANIUM-RICH ORES

BACKGROUND OF THE INVENTION

The invention relates to the hydrocyanation of either 2-pentenenitrile, 3-pentenenitrile, 4-pentenenitrile, 2-methyl-3-butenenitrile, or mixtures thereof to produce adiponitrile (ADN) and/or 2-methylglutaronitrile (MGN) using a zero-valent nickel catalyst promoted by a byproduct of the chlorination of titanium-rich ores.

U.S. Pat. No. 3,496,217, issued in 1970, discloses an improvement in hydrocyanation using a large number of metal cation compounds with a variety of anions as catalyst promoters. U.S. Pat. No. 3,925,445, issued in 1975, discloses zero-valent nickel hydrocyanation catalysts promoted with metal halides and organoboron compounds. U.S. Pat. No. 4,774,353, issued in 1988, discloses zero-valent nickel hydrocyanation catalysts promoted with triorganotin compounds. U.S. Pat. No. 4,874,884, issued in 1989, discloses zero-valent hydrocyanation catalysts promoted using a synergistic combination of promoters. U.S. Pat. No. 6,048,996, issued in 2000, discloses zero-valent hydrocyanation catalysts promoted using an insoluble Lewis acid promoter.

SUMMARY OF THE INVENTION

The present invention provides a process for the preparation of adiponitrile by the addition of hydrogen cyanide to either 2-pentenenitrile, 3-pentenenitrile, 4-pentenenitrile, or mixtures thereof in the presence of a zero-valent nickel catalyst, and a promoter obtained as a byproduct from the chlorination of titanium-rich ores. This byproduct comprises iron (II) chloride and manganese (II) chloride. The crude byproduct can be used directly in the hydrocyanation reaction without separation steps.

The present invention also provides a process for the preparation of 2-methylglutaronitrile by the addition of hydrogen cyanide to 2-methyl-3-butenenitrile in the presence of a zero-valent nickel catalyst, and a promoter obtained as a byproduct from the chlorination of titanium-rich ores, comprising iron (II) chloride and manganese (II) chloride.

In the present invention, the preparation of adiponitrile and the preparation of 2-methylglutaronitrile may be performed in separate processes or may be performed concurrently in the same process.

DETAILED DESCRIPTION OF THE INVENTION

The present invention can be employed to produce a variety of nitriles. Of particular interest is adiponitrile (ADN) because it is an intermediate used in the production of hexamethylenediamine, which, in turn, is used to produce polyhexamethyleneadipamide (nylon-6,6), a commercial polyamide useful in forming fibers, films, and molded articles. ADN may also serve as a precursor for production of caprolactam, which is used to produce polycaprolactam (nylon-6), via a process involving partial hydrogenation of adiponitrile. Accordingly, a preferred embodiment of the invention is a process which comprises reacting either 2-pentenenitrile, 3-pentenenitrile, 4-pentenenitrile, or mixtures thereof with HCN to produce ADN in the presence of a zero-valent nickel catalyst and a promoter obtained as a byproduct from a titanium ore chlorination process.

Also of interest is 2-methylglutaronitrile(MGN), which is an intermediate useful for the production of modified nylon-6,6 and nylon-6 polymers. Thus, another embodiment of the present invention is a process which comprises reacting 2-methyl-3-butenenitrile with HCN to produce MGN in the presence of a zero-valent nickel catalyst and a promoter obtained as a byproduct from a titanium ore chlorination process.

A further embodiment of the present invention is a process in which both ADN and MGN are produced via the hydrocyanation of mixtures of pentenenitriles, in any and all proportions, in the presence of a zero-valent nickel catalyst and a promoter obtained as a byproduct from a titanium ore chlorination process.

The catalysts employed for this process include complexes of zero-valent nickel with ligands such as phosphines, arsines, stibines, phosphites, arsenites, stibites and mixtures thereof. Ligand may be added in excess of what can theoretically be coordinated to the nickel at a given time. The use of excess ligand may improve stability for the nickel catalyst. The catalysts may be preformed or prepared in situ in the hydrocyanation reaction environment.

A preferred group of these Ni(0) catalysts have the general structure:

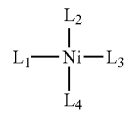

wherein $L_1$, $L_2$, $L_3$, and $L_4$ are neutral ligands which may be the same or different and have the formula P(XYW) wherein X and Y are selected from the group consisting of R and OR', and W is OR", wherein R, R', and R" may be the same or different, and wherein R, R', and R" are selected from the group consisting of alkyl and aryl groups containing up to 18 carbon atoms, with aryl being preferred. Alkyl groups may be linear or branched. A particularly preferred group within the foregoing zero-valent nickel catalysts is that disclosed in U.S. Pat. No. 3,903,120. This preferred group of catalysts can be described by the general formula $NiL_4$, where L is a neutral ligand such as a triarylphosphite of the formula $P(OAr)_3$, wherein Ar is an aryl group of up to 18 carbon atoms. Illustrative of the aryl groups are methoxyphenyl, tolyl, xylyl, and phenyl. Preferred aryl groups are meta-tolyl, para-tolyl, and phenyl, and mixtures thereof.

Suitable ligands for the present invention are also bidentate phosphorous-containing ligands selected from the group consisting of bidentate phosphites and bidentate phosphinites. Preferred ligands are bidentate phosphite ligands.

The preferred bidentate phosphite ligands are of the following structural formulae:

$(R^1O)_2P(OZO)P(OR^1)_2$,     I

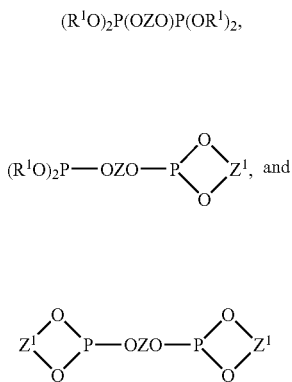

In formulae I, II and III, $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the group consisting of structural formulae IV, V, VI, VII, and VIII:

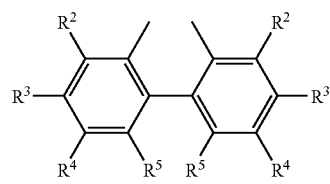

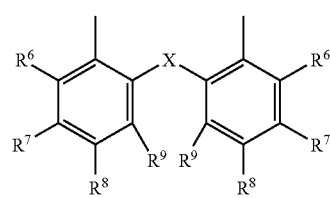

wherein:
$R^2$, $R^3$, $R^4$, $R^5$, $R^6$, $R^7$, $R^8$, and $R^9$ are independently selected from H, $C_1$ to $C_{12}$ alkyl, and $C_1$ to $C_{12}$ alkoxy;
X is O, S, or $CH(R^{10})$;
$R^{10}$ is H or $C_1$ to $C_{12}$ alkyl;

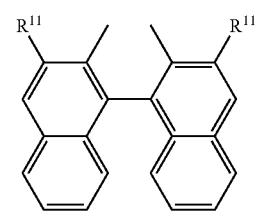

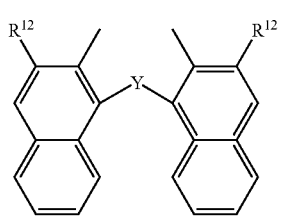

wherein:
$R^{11}$ and $R^{12}$ are independently selected from H, $C_1$ to $C_{12}$ alkyl, $C_1$ to $C_{12}$ alkoxy, and $CO_2R^{13}$;
$R^{13}$ is $C_1$ to $C_{12}$ alkyl or $C_6$ to $C_{10}$ aryl, unsubstituted or substituted with $C_1$ to $C_4$ alkyl;
Y is O, S, $CH(R^{14})$;
$R^{14}$ is H or $C_1$ to $C_{12}$ alkyl;

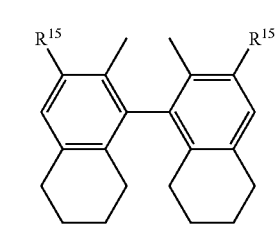

wherein:
$R^{15}$ is selected from H, $C_1$ to $C_{12}$ alkyl, $C_1$ to $C_{12}$ alkoxy, and $CO_2R^{16}$;
$R^{16}$ is $C_1$ to $C_{12}$ alkyl or $C_6$ to $C_{10}$ aryl, unsubstituted or substituted with $C_1$ to $C_4$ alkyl.

In the structural formulae I through VIII, the $C_1$ to $C_{12}$ alkyl and $C_1$ to $C_{12}$ alkoxy groups may be straight chains or branched.

Examples of bidentate phosphite ligands that are useful in the present process include those having the formulae IX to XXXII, shown below wherein for each formula, $R^{17}$ is selected from the group consisting of methyl, ethyl or isopropyl, and $R^{18}$ and $R^{19}$ are independently selected from H or methyl:

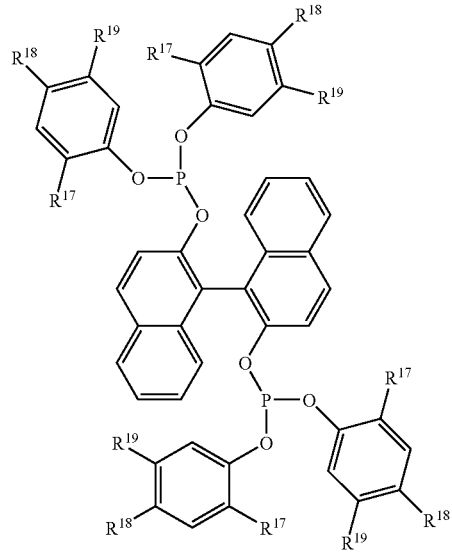
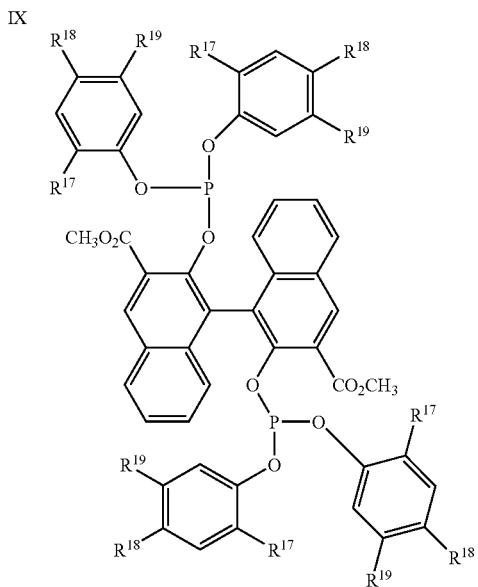
IX
X
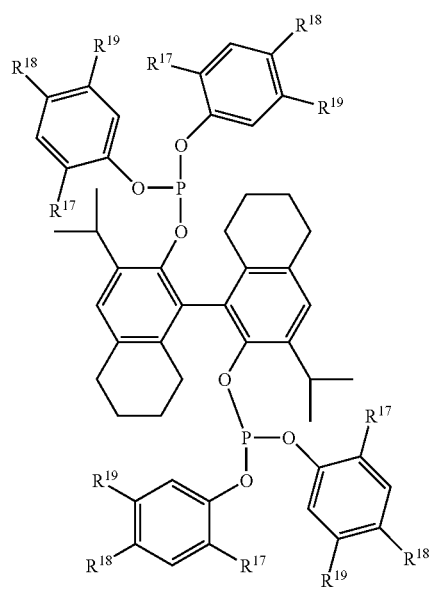
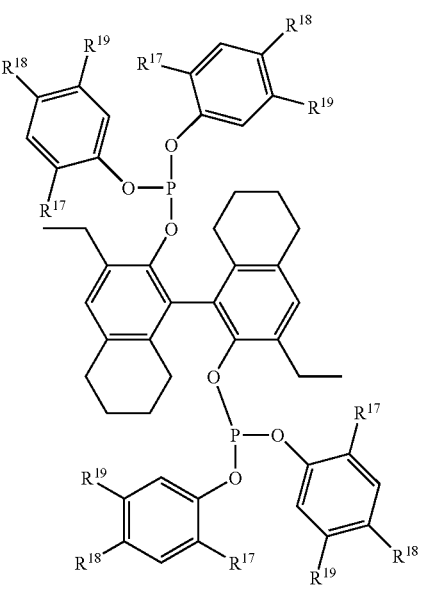
XI
XII

-continued
XIII
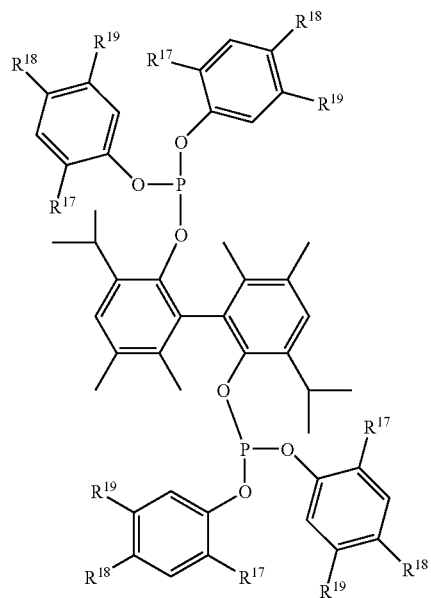
XIV
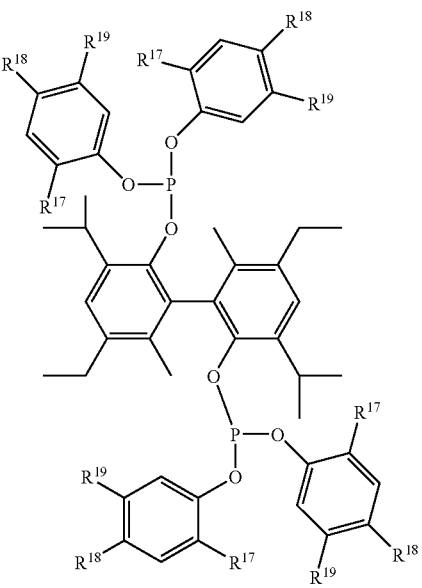
XV
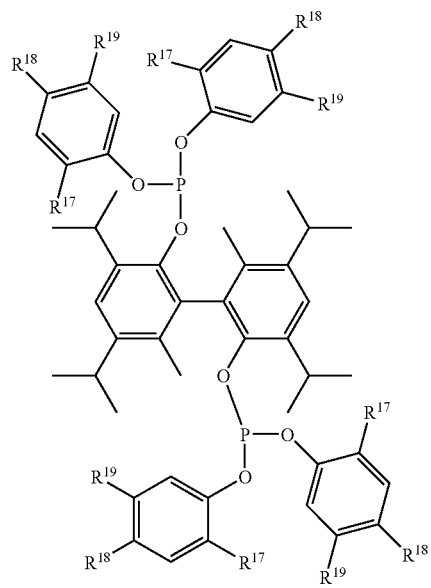
XVI
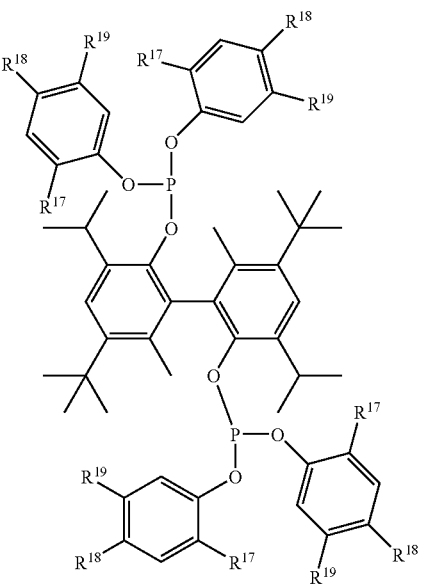

-continued
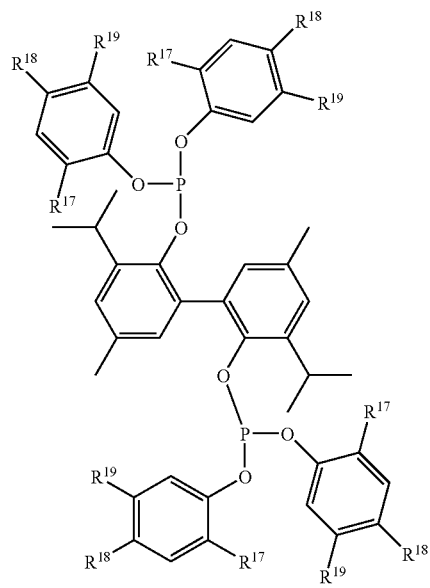
XVII
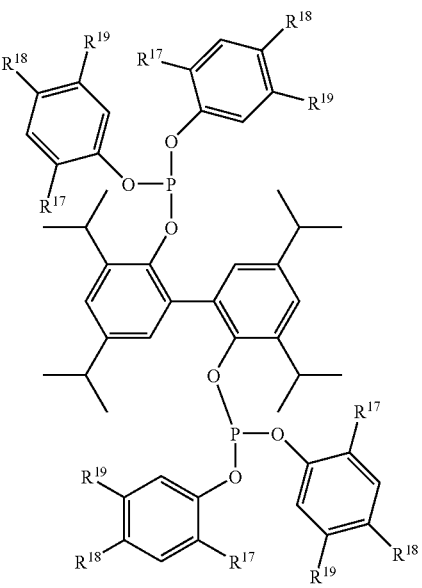
XVIII
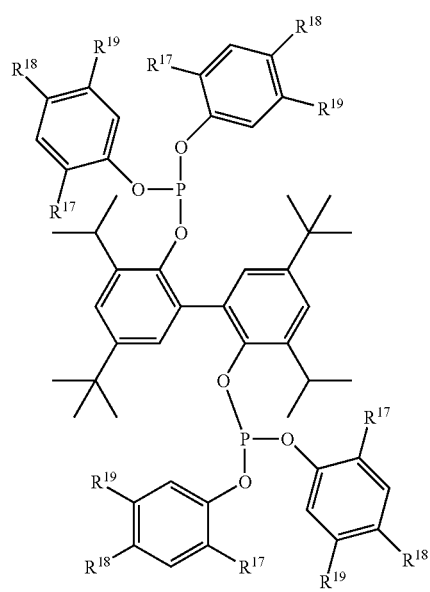
XIX
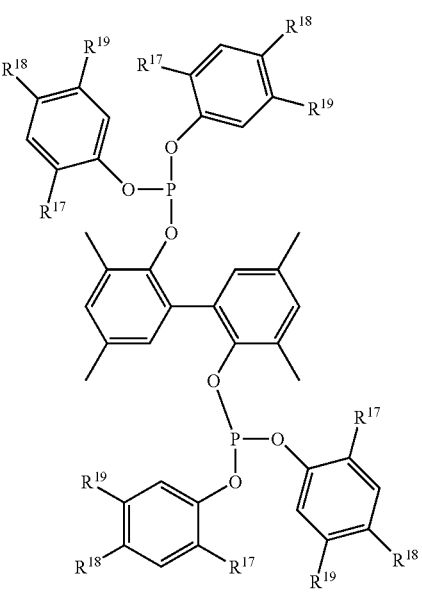
XX

-continued
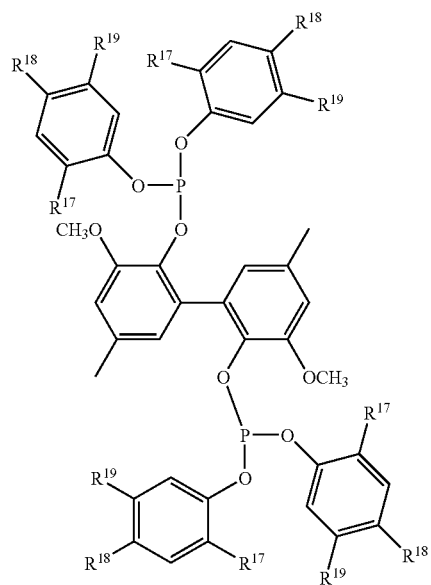
XXI
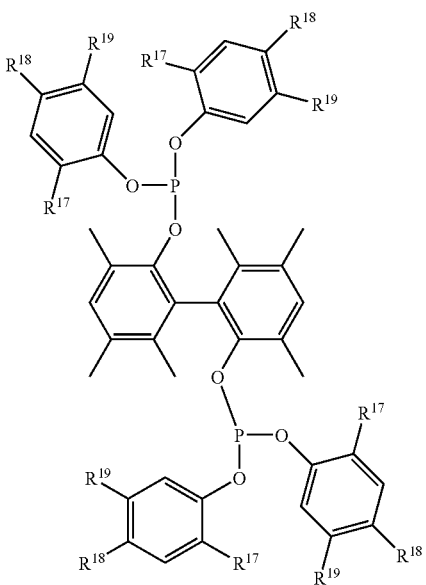
XXII
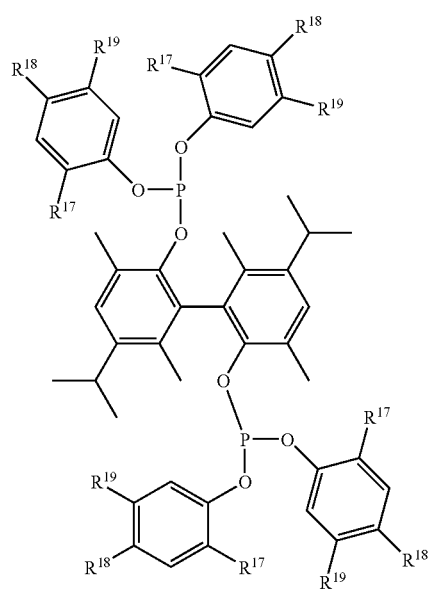
XXIII
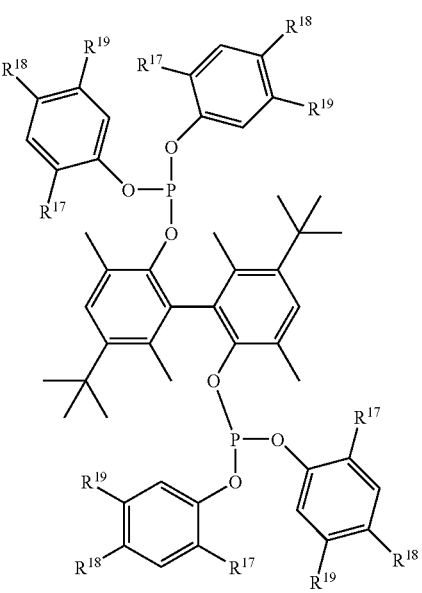
XXIV

-continued
XXV
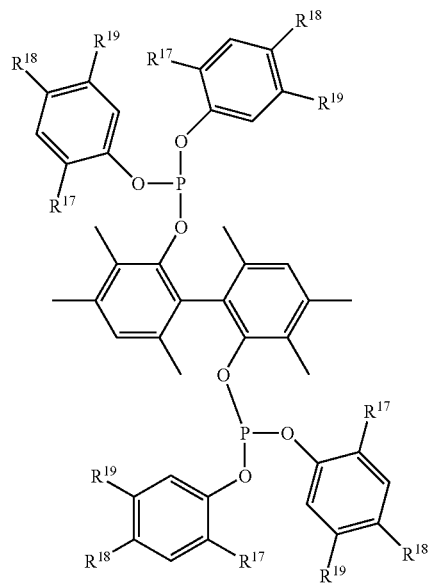
XXVI
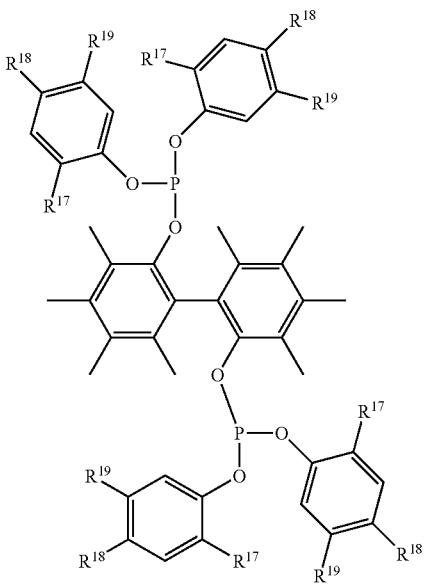
XXVI
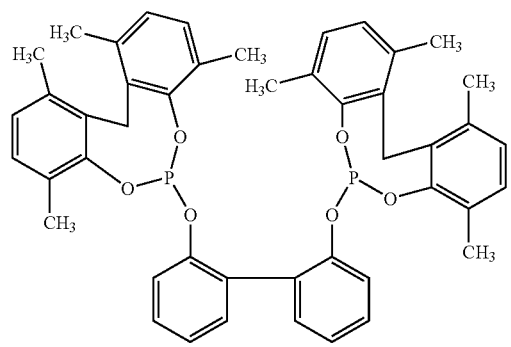
XXVIII
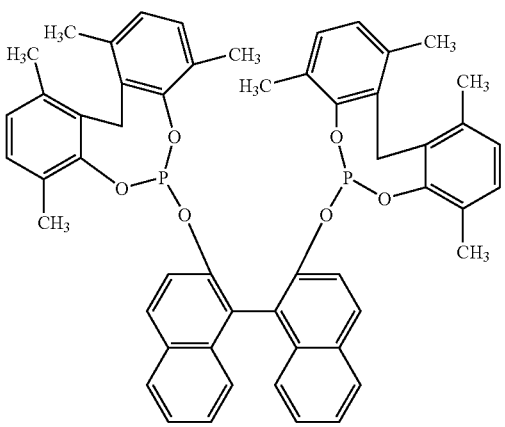
XXIX
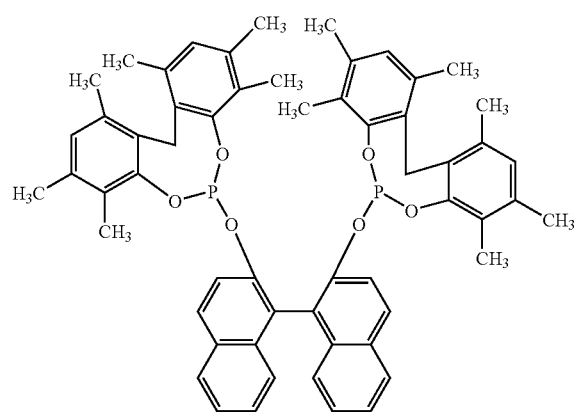
XXX
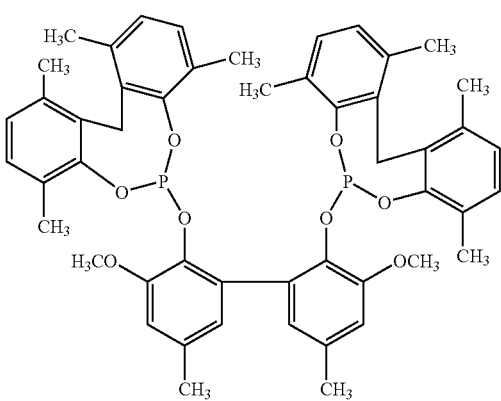

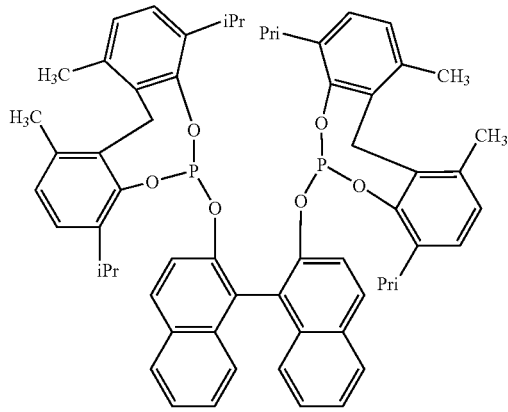
XXXI

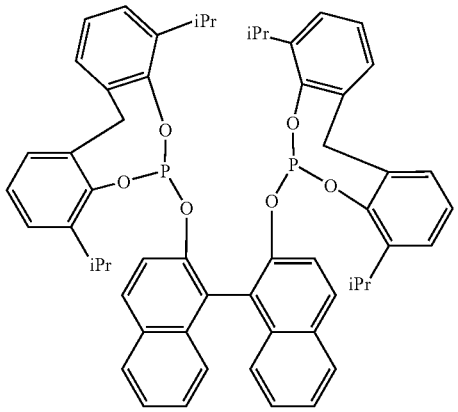
XXII

Suitable bidentate phosphites are of the type disclosed in U.S. Pat. Nos. 5,512,695; 5,512,696; 5,663,369; 5,688,986; 5,723,641; 5,847,191; 5,959,135; 6,120,700; 6,171,996; 6,171,997; and 6,399,534. Suitable bidentate phosphinites are of the type disclosed in U.S. Pat. Nos. 5,523,453 and 5,693,843.

The promoter of the present invention is a byproduct obtained from a chlorination process of titanium-rich ores.

In the production of titanium tetrachloride, raw materials, including ilmenite or rutile ores or other titanium-rich materials such as those obtained from beneficiating these ores, are reacted with chlorine under reducing conditions to yield a mixture of metal chlorides from which titanium tetrachloride may be recovered. Iron chloride is present in the chlorination product of practically every case where iron-containing ores are used in the raw materials. Iron in the form of compounds or complexes is often present in titanium-containing materials that are chlorinated. Often such iron material will be present in an amount of about 0.5 to 50 percent by weight A major amount of the iron material typically is present as iron oxide. The iron compounds in the titanium-containing material typically react to form iron chloride, which can be present in the form of ferrous chloride or ferric chloride. In addition, other metal chlorides, such as manganese or vanadium chloride, can be present in these mixtures to a smaller extent. A typical chlorination process is described in U.S. Pat. No. 5,585,078.

In particular, a process of chlorinating titanium-containing material in a fluidized bed reactor is known. Suitable processes are disclosed in U.S. Pat. Nos. 2,701,179; 3,883,636; and 2,446,181. In such processes, particulate coke, particulate titanium-bearing material, chlorine and optionally oxygen or air are fed into a reaction chamber, and suitable reaction temperatures, pressures and flow rates are maintained to sustain the fluidized bed. Gaseous titanium tetrachloride and other metal chlorides, such as iron-based chlorides, are exhausted from the reactor chamber. The gaseous titanium tetrachloride so produced can then be separated, leaving behind a byproduct material that can be used as the promoter in the present invention.

Typical conditions and specifications for fluidized beds useful for this invention are as follows; reaction temperature of about 900 to 1300° C., pressure of about 1.5 to 3 atmospheres, reactor size of about 6 to 25 feet in diameter with multiple chlorine jets in or near the base, reactor superficial velocity of about 0.5 to 1.5 feet per second, and a settled bed depth of about 6 to 25 feet. Typically, the titanium-containing material initially fed has a particle size of about 70 to 800 microns in diameter, and the coke initially fed has a particle size of about 300 to 3000 microns in diameter. Preferably, the chlorine jets will be located within 0 to 10 feet of the base of the reactor.

The titanium-bearing material can be any titanium source materials such as titanium-containing ores including rutile, ilmenite or anatase ore; beneficiates thereof; titanium containing by-products or slags; and mixtures thereof. Ordinarily, the titanium-bearing material contains iron oxide in an amount of about 0.5 to 50 percent by weight and preferably up to about 20 percent by weight.

A chlorination process that produces the byproduct promoter of this invention is the procedure described in U.S. Pat. No. 4,961,911. A fluidized bed reactor can be operated at a temperature of 1000° C. This reactor is fed with an ore blend, containing approximately 74% $TiO_2$ and 21.5% iron oxides and 4.5% other impurities, and with coke. A fluidizing gas is fed to a distributor at the bottom of the reactor and consists of about 75% chlorine and a diluent gas consisting primarily of nitrogen, hydrogen chloride, oxides of carbon and oxygen. The ore, coke and fluidizing gas are fed to the reactor at rates of 100 to 200 pounds per hour per square foot of reactor cross-sectional area, respectively. A stream of about 20 pounds of crude titanium tetrachloride per hour per square foot of reactor cross-sectional area is fed about 5 feet above the level of the static bed. The gases leaving the chlorinator contain the following typical components in the following typical percentages by volume: titanium tetrachloride 22%, iron chloride 7%, carbon dioxide 23%, carbon monoxide 3%, nitrogen 36 %, hydrogen chloride 7% and chlorine 0.03%. The off-gas titanium tetrachloride is directed to a cooling train and collected.

A method to obtain the by-product promoter of this invention from this chlorination process of titanium-rich ores is illustrated by a procedure described in U.S. Pat. No. 4,994,255. This procedure illustrates a general method and can be modified as needed by those skilled in the art. The $FeCl_2$ formed in the entrained-flow beneficiator after the chlorination process is separated from crude titanium dioxide in a series of cyclone separators connected by conduits. The gaseous ferrous chloride is quenched with cooling liquid titanium tetrachloride introduced through an inlet. This causes the ferrous chloride to solidify, whereby it is conducted as solid particulate ferrous chloride through another conduit into a collection vessel from which the by-product promoter of the invention can be collected. This vessel can also function as a direct feed for a ferrous chloride oxidizer, where the further oxidation to ferrous oxide to recycle chlorine gas can be practiced. The byproduct (containing iron chloride) produced and collected in this manner can be used as the promoter in the hydrocyanation process of this invention.

The hydrocyanation reaction can be carried out by charging a reactor with all of the reactants or preferably charging the reactor with the catalyst, or catalyst components, the desired mixture of pentenenitriles and/or 2-methyl-3-butenenitrile, the byproduct promoter, and whatever solvent is used and then sweeping hydrogen cyanide gas over the surface of the reaction mixture or bubbling it through the reaction mixture. Another technique is to charge the reactor with the catalyst, the byproduct promoter, hydrogen cyanide and whatever solvent is to be used and feed the desired mixture of pentenenitriles and/or 2-methyl-3-butenenitrile slowly to the reaction mixture. Preferably, the hydrocyanation is conducted continuously in one or more agitated steps or stages. The hydrocyanation reaction can be carried out with or without a solvent. The byproduct promoter of this invention can be charged to the hydrocyanation reaction mixture either in a solvent or in a mixture of the nitriles. The byproduct promoter can be added homogeneously, dissolved in either a solvent or a mixture of the nitriles, or it can be added as a slurry. The byproduct promoter can be added to the hydrocyanation reaction mixture without prior purification or separation.

A typical byproduct promoter contains iron (II) chloride and smaller amounts of manganese (II) chloride and other by-product metal chlorides to a much smaller extent, in addition to other materials such as sand or coke. Some of the components of this byproduct promoter are not soluble in solvents for the hydrocyanation process or in mixtures of the substrate nitriles. The byproduct promoter can be added to the hydrocyanation reaction mixture either directly as a solid; or as a slurry in either a hydrocyanation solvent or a mixture of nitriles; or as a homogeneous solution after filtration from materials which are not dissolved in the mixture of substrate nitriles or solvent. Typical methods of filtration applicable to the present invention are taught in Peny's Chemical Engineers' Handbook, McGraw-Hill Publishing Company.

EXAMPLE

The following non-limiting, representative example illustrates the process of this invention. All parts, proportions, and percentages are by weight, unless otherwise indicated.

Catalyst solutions were prepared by mixing a phosphite ligand and Ni(COD)$_2$ ("COD" means 1,5-cyclooctadiene) in a molar ratio of 1.1:1 and dissolving this in toluene. The byproduct promoter was added to trans-3-pentenenitrile (t-3PN), and the mixture was agitated. After filtration from insoluble material, the solution was used without further treatment in the hydrocyanation reaction. To the catalyst solution was added a solution of the byproduct promoter in the substrate t-3PN. The molar ratio of t-3PN to Ni was 200. The catalyst solution and the solution of the promoter mixture in t-3PN were combined to form a homogeneous reaction mixture. The reaction vessel was placed in a reactor and hydrogen cyanide, placed in a reservoir attached to the reactor, was delivered by slow evaporation of the hydrogen cyanide into the reactor vessel. The reaction was run for 24 hours at 50 degrees C., after which time all hydrogen cyanide had been consumed. The reaction mixture was analyzed using standard gas chromatographic techniques.

The following bidentate phosphite ligand was used in this example:

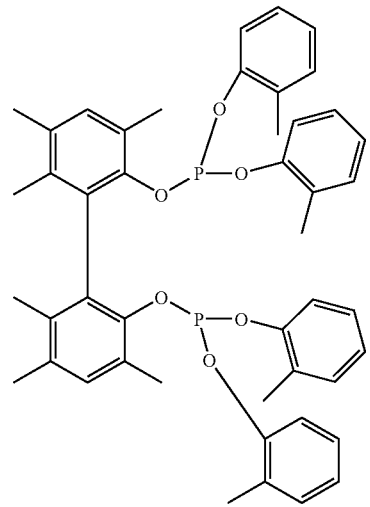

The conversion of t-3PN to dinitriles was 92.8%, and the ratio of adiponitrile over the sum of all dinitriles was 96.1%.

What is claimed is:

1. A process for hydrocyanation of at least one substrate selected from the group consisting of 2-pentenenitrile, 3-pentenenitrile, 4-pentenenitrile, and 2-methyl-3-butenenitrile comprising contacting the substrate with hydrogen cyanide in the presence of a zero-valent nickel hydrocyanation catalyst and a promoter, wherein said promoter is a byproduct of a method for producing titanium tetrachloride from titanium ore, said method comprising the steps of contacting a titanium-containing ore with chlorine under reducing conditions to obtain a gaseous reaction product, recovering titanium tetrachloride from the reaction product, thereby leaving behind a residue, and condensing the residue to obtain said byproduct, and wherein said byproduct consists essentially of iron (II) chloride, manganese (II) chloride, sand, and coke.

2. A process comprising:
 a) chlorinating a titanium-containing material, wherein the titanium-containing material contains iron oxide in an amount of about 0.5 to 50 percent by weight, to produce a mixture of metal chlorides comprising titanium tetrachloride and other iron-based chlorides;
 b) separating the titanium tetrachloride;
 c) obtaining a byproduct material consisting essentially of iron (II) chloride, manganese (II) chloride, sand, and coke;
 d) using the byproduct material as a promoter in a process for hydrocyanation, said hydrocyanation process comprising contacting at least one substrate selected from the group consisting of 2-pentenenitrile, 3-pentenenitrile, 4-pentenenitrile, and 2-methyl-3-butenenitrile with hydrogen cyanide in the presence of a zero-valent nickel hydrocyanation catalyst and the promoter.

3. The process of claim 2, wherein the substrate is 2-pentenenitrile.

4. The process of claim 2, wherein the substrate is 3-pentenenitrile.

5. The process of claim 2, wherein the substrate is 4-pentenenitrile.

6. The process of claim 2, wherein the substrate is 2-methyl-3-butenenitrile.

7. The process of claim 2, wherein chlorinating a titanium-containing material is performed in a fluidized bed reactor.

8. The process of claim 2, wherein the byproduct material is used in a process for hydrocyanation without prior purification or separation.

9. The process of claim 2, wherein the nickel hydrocyanation catalyst comprises a bidentate phosphite ligand.

10. The process of claim 1, wherein the nickel hydrocyanation catalyst comprises the bidentate phosphite ligand having the formula.

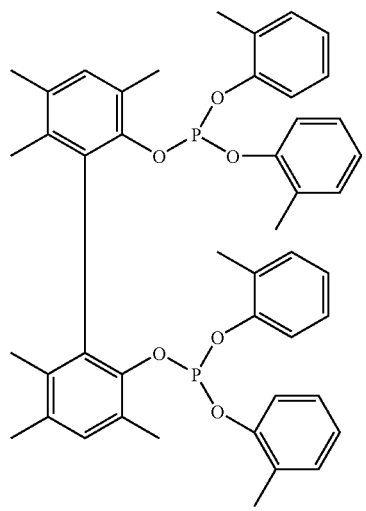

11. A process comprising:
reacting 2-methyl-3-butenenitrile with hydrogen cyanide to produce 2-methylglutaronitrile in the presence of a zero-valent nickel catalyst and a promoter obtained as a byproduct from a titanium ore chlorination process, wherein said byproduct consists essentially of iron (II) chloride, manganese (II) chloride, sand, and coke.

12. A process comprising:
reacting a mixture of pentenenitriles with hydrogen cyanide to produce both adiponitrile and 2-methylglutaronitrile in the presence of a zero-valent nickel catalyst and a promoter obtained as a byproduct from a titanium ore chlorination process, wherein said byproduct consists essentially of iron (II) chloride, manganese (II) chloride, sand, and coke.

13. The process of claim 2, wherein the titanium-containing material is rutile ore; ilmenite ore; anatase ore; beneficiates of rutile, ilmenite, or anatase ore; titanium containing by-products or slags; and mixtures thereof.

14. The process of claim 2, wherein in step d) the byproduct material is added to the hydrocyanation reaction mixture directly as a solid, or as a slurry in either a hydrocyanation solvent or a mixture of nitriles, or as a homogeneous solution after filtration from materials which are not dissolved in the mixture of substrate nitriles or solvent.

* * * * *